United States Patent

Wang et al.

[11] Patent Number: 4,950,835
[45] Date of Patent: Aug. 21, 1990

[54] NOVEL SILICON-MODIFIED CATALYST SI/HZSM-5, IT'S PREPARATION, AND A PROCESS FOR SYNTHESIZING HIGH PURITY P-DIALKYL BENZENE FROM MONOALKYL BENZENE BY USING SAID CATALYST

[75] Inventors: Ikai Wang; Biing-Jye Lee; Mei-Hwei Chen, all of Hsinchu, Taiwan

[73] Assignee: Taiwan Styrene Monomer Corporation, Taipei, Taiwan

[21] Appl. No.: 426,741

[22] Filed: Oct. 24, 1989

[51] Int. Cl.$^5$ .............................................. C07C 2/68
[52] U.S. Cl. .................................... 585/467; 585/475
[58] Field of Search ........................................ 585/467

[56] References Cited

U.S. PATENT DOCUMENTS 4,849,386 7/1989 Wang et al. ........................ 502/62

FOREIGN PATENT DOCUMENTS 0289691 of 0000 European Pat. Off. .

Primary Examiner—Curtis R. Davis
Attorney, Agent, or Firm—Ladas & Parry

[57] ABSTRACT

This invention relates to the preparation of a novel Si/HZSM-5 catalyst through vapor phase deposition of Si on the surface of HZSM-5 catalyst which is obtained by ion exchanging ZSM-5 catalyst. The source of deposition Si comes from tetraalkyl ortho-silicate (or tetraalkoxy silane), Si(OR)4, wherein R represents the alkyl group that contains 1-4 carbon atoms. The silicon deposit will substantially not clog the pores of the catalyst.

The present invention is to make use of the modified catalyst in the alkylation or disproportionation reactions in order to enhance the yield of p-dialkylbenzene as an ingredient in the final product of aryl compounds such as toluene or ethylbenzene.

7 Claims, 8 Drawing Sheets

NOVEL SILICON-MODIFIED CATALYST SI/HZSM-5, IT'S PREPARATION, AND A PROCESS FOR SYNTHESIZING HIGH PURITY P-DIALKYL BENZENE FROM MONOALKYL BENZENE BY USING SAID CATALYST

FIELD OF THE INVENTION

The present invention relates to a novel method to produce Si/HZSM-5 catalyst and to use it in enhancing the output ration of p-dimethylbenzene, p-diethylbenzene or p-ethyl-toluene through the alkylation or disproportionation of toulene and ethylbenzene

BACKGROUND OF THE INVENTION

Dialkylbenzenes, including xylene, diethylbenzene and ethyltoluene, all have three sorts of isomers, namely p-, o- and m-dialkylbenzene. As their industrial application, generally speaking, they can be used as organic solvent, resin bridging agent and can serve as a starting material of other specialized chemicals. Generally speaking, p-dialkylbenzene has a broad spectrum of usage more than their isomers. p-diethylbenzene can be directly used as the releasing agent in the course of separation of xylenes and therefore, it is a chemical with potent high added value. The dehydrogenated product of p-methylstyrene can be polymerized, and the so-obtained polymer can in many respect displace the polystyrene, thus lessening the consumption of benzene and alleviating the shortage of benzene. Meanwhile, poly-p-methylstyrene uses directly the toluene as raw material, thus saving the consumption of hydrogen in the course of producing benzene from toluene through the process of hydrogenation and dealkylation and thus lowering the cost.

Dialkylbenzene can conventionally be synthesized by using the existing alkylation catalyst e.g, $AlCl_3$—HCl and the unmodified ZSM-5. However, the conventional catalyst is void of selectivity to isomers. Therefore, the isomers of the aforesaid o-, m-, p-dialkylbenzenes can be resulted according to the ratio of thermodynamics. For instance, ethyltoluene is generated by the alkylation of ethylene and toluene. The equilibrium ratio in the thermodynamics is given as follows:

o-ethyltoluene: m-ethyltoluene: p-ethyltoluene = 16.3%: 49.9%: 33.7% (600° K.)

As the boiling point of isomers closely approximates to one another, the relative volatility comes near 1. The separation is therefore difficult and the cost of operation is quite expensive. If $AlCl_3$—HCl is used as the catalyst, not only separation is difficult but it is also impossible to avoid the loss of raw material due to multiple alkylation. Moreover, such a catalyst is liable to cause serious problems of pollution and corrosion due to its strong acidity.

The Mobil Petroleum Corporation of the United States developed, in 1972, a new type of catalyst, which is known as ZSM-5. The particulars of the method of production were disclosed as per U.S. Pat. No. 3,702,886. The crystal structure of ZSM-5 catalyst has a specific order of arrangement and is a porous aluminum silicate crystal. The pores of this sort of catalyst has a homogeneous pore size and, therefore, some smaller than average particles are adsorbable and larger particles are repelled. Hence, it would be frequently referred to as "molecular sieve". There are many precedents in the industry in making use of this characteristics to conduct chemical reactions. The ZSM-5 catalyst is characterised by its selectivity, being able to satisfy the needs for high selectivity to product of different molecules, but its selectivity still falls short of expectations in the way of isomers of the same kind of product. For instance, when methyl alcohol and toluene are reacted over ZSM-5 catalyst, both the rate and the selectivity is very high for xylenes, but the ratio among the isomers of o-, m-, p-xylene remains near the equilibrium value in thermodynamics (refer to W. W. Kaeding, C. Chu, L. B. Yound, B. Weinstein, S. A. Butter, Journal of Catalysis, 67, p.159, 1981).

The ZSM-5 catalyst is a zeolite with high contents of silicon dioxide. Its silicon/aluminum ratio ranges from 20 to 10,000 or more. Its crystal system is $(TPA)_2O$—$Na_2O$—$K_2O$—$Al_2O_3$—$SiO_2$—$H_2O$. In preparing this kind of catalyst the water solution containing tetrapropylammonium compound, sodium oxide, aluminum oxide, silicon oxide, is usually employed in a specific ratio, the composition is hermetically sealed for heating at 100° C. to 175° C. for a period of from six hours to 60 days to make possible the crystallization. The size of crystal particles, the ratio and specific characteristics of ingredients vary with the conditions of the reaction. The cation of the primitive catalyst such as $TPA^+$, $Na^+$ and $K^+$ can be transferred into some other cations through the well-known techniques of ion exchange. The usually used substituants for cation are hydrogen ion, rare earth element ions, manganese ion and the ions of the Group II or VIII elements in the periodic table.

As commonly known in the art the modification of catalyst could be accomplished by means of impregnation, poisoning of the active sites on external surface and steam treatment. Among these treatments, the impregnation process is most effective. The term "impregnation process" refers to the immersion of a ZSM-5 catalyst in a solution containing magnesium, phosphorus, boron or silicon- compounds and then air-dried and calcined to convert the compounds into oxides, thus obtaining a modified catalyst. Take, for example, the modification through the magnesium impregnation. The ammonium-contained $NH_4ZSM$-5 catalyst or hydrogen-contained HZSM-5 catalyst obtained after ion-exchanging is slurried in aqueous solution of magnesium acetate and is then heated at 70°–95° C. and allowed to stand overnight. The viscous solution is placed in a crystalizing dish and dried in an oven at a relatively high temperature of about 120° to 200° C. for about 10 hours. Finally it is calcined overnight at a temperature as high as about 500°–550° C. As a result, the modified catalyst through immersion with adequate contents of magnesium is obtained. For phosphorous-modified catalyst, the solution of phosphoric acid, diammonium acid phosphate or trialkyl phosphine is used. the boiling point of such a solution is low. Therefore, the immersion is usually carried out at room temperature for a longer than average period of time, or otherwise, it may be distilled for a longer than average period of time with reflux column. Then, it is over dried slowly and calcined later on. However, the catalyst as modified through impregnation is reduced by far in activity and regenerability as demerits. Besides, during the synthesis of ZSM-5 catalyst, a slight difference in the operational conditions (such as the feeding of material, mixing of temperature, etc.) may oftenly result in significant difference in the performance of ZSM-5 catalyst, for each lot of the yield. Therefore, the modification of the catalyst through impregnation may oftenly make it impossible to render a judgment of the optimum amount of the modifier.

SUMMARY OF THE INVENTION

Figure 1:
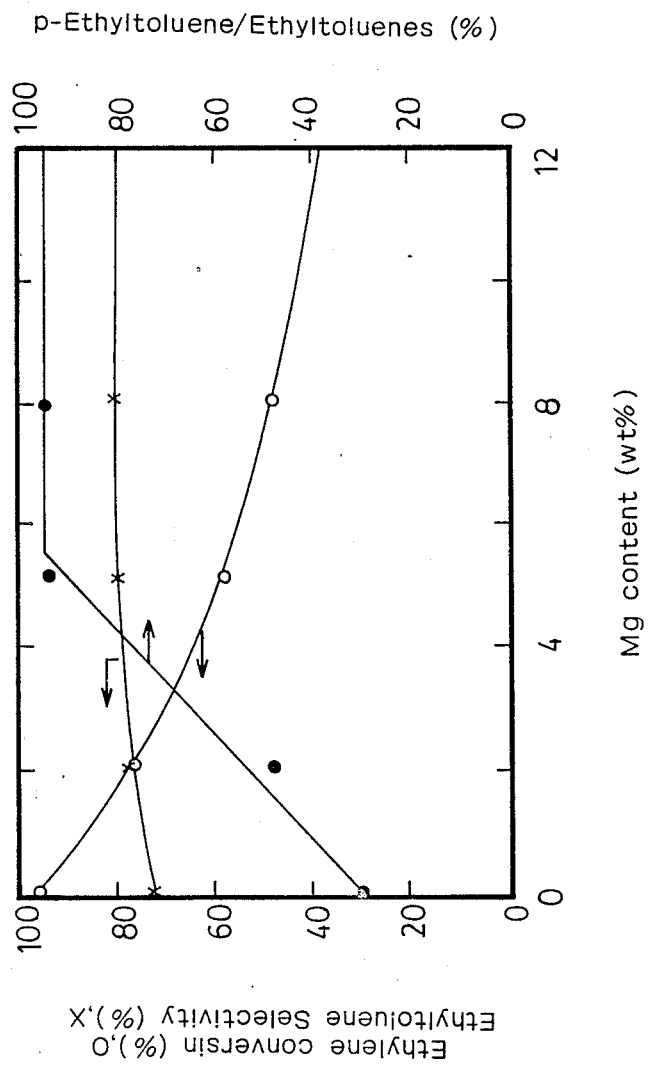
FIG. 1 Effect of different impregnating contents on reaction activity and selectivity to product FIG. 2 A comparison of activity between the magnesium-immersed catalyst and the catalyst modified by Si deposition during reaction FIG. 3 Effect of volume of Si(OC$_2$H$_5$) added on Activity of alkylation and selectivity to product FIG. 4 A comparison of activity on different particle size of modified ZSM-5 catalyst FIG. 5 Long-term test on the modified Si/HZSM-5 catalyst, after its first regeneration in a disproportionation reaction to p-ethylbenzene (large particles, without binder)

This invention is to modify ZSM-5 catalyst through the vapor phase deposition method so as to obtain a novel Si/HZSM-5 catalyst and, by making use of such a modified catalyst, the percentage of the content of p-dialkylbenzene may be enhanced in the yield of dialkylbenzenes.

DETAILED DESCRIPTION OF SPECIFIC EMBODIMENT

The novel Si/HZSM-5 catalyst under this invention is prepared by first ion-exchanging the catalyst ZSM-5 into catalyst HZSM-5, to which is in turn deposited on with tetra alkyl orthosilicate by means of vapor phase deposition. Included in the deposition process are the pulsating type vapor phase deposition previous to the reaction and the pulsating type vapor phase deposition during the reaction and the continuous type deposition before reaction and that during reaction. The source of Si supply is tetra-alkyl orthosilicate, Si(OR)$_4$, wherein R represents the alkyl group of 1-4 carbon. The silicon deposit substantially will not clog the pores of the catalyst, as one of the features.

The present invention also uses the modified catalyst to promote the alkylation or disproportionation reactions of aryl compounds such as toluene or ethylbenzene so as to elevate the contents of p-dialkylbenzene in the yield of dialkylbenzenes.

The method under this invention is applicable all the same to elevate the percentage of p-dialkylbenzene in the yield of dialkylbenzenes, either (1) in the case of xylene obtained through disproportionation of toluene, or obtained through the alkylation of methanol and toluene; or (2) in the case of diethylbenzene obtained through the disproportionation of ethylbenzene or otherwise obtained through the alkylation of a combination of ethylene, ethanol, and ethylbenzene; or (3) in the case of ethyltoluene as obtained through the alkylation of ethylene and toluene or that of ethanol and toluene. The reaction may proceed by contacting with Si/HZSM-5 catalyst at a temperature of from 200° to 500° C., a weight hourly space velocity of from 0.5–100 per hour (WHSV) and a pressure of from 0–1,000 psig. The distribution of the reaction products is mainly concentrated to the desired p-dialkylbenzene Generally speaking, the size of the particles of the modified catalyst as used in the course of the reactions ranges from 0.01 to 30 $\mu$m and the ratio of SiO$_2$/Al$_2$O$_3$ is larger than 20.

While ZSM-5 catalyst, as the precursor catalyst of Si/HZSM-5 catalyst, is processed through the well-known techniques, including, those steps as ion exchange, drying, calcination, etc., However, the present invention is to use the newly developed vapor phase deposition. This, in combination with the specialized physical properties inherent to ZSM-5 catalyst, can enhance the ratio of selectivity to product of p-dialkylbenzene, as a novel method that is highly effective. The following examples can best illustrate the process of this invention.

EXAMPLE 1

Modification of the conventional ZSM-5 catalyst by impregnation with magnesium:

The HZSM-5 after going through ion exchange is immersed in Mg(CH$_3$COO)$_2$. 4H$_2$O solutin of appropriate concentration for 24 hours and then is dried in a 100° C. oven. The catalyst is further calcined at 500° C. for 15 hours. In this manner, the impregnated compound is converted to oxide.

EXAMPLE 2

The reactivity of mangesium-impregnated catalyst:

Following the procedure given in Example 1 above, ZSM-5 catalyst with different contents of magnesium (SiO$_2$/Al$_2$O$_3$=90) is used in the course of the reaction of ethylene and toluene. When the temperature of the reaction reaches 320° C., the changing status of the conversion of ethylene and the selectivity of p-ethyltoluene along with the magnesium content is given in FIG. 1. As indicated in the figure, the ratio of selectivity to product of p-ethyltoluene is elevated rapidly in proportion to the increase in the contents of magnesium and then is leveled off. The conversion ratio of ethylene falls gradually with the increase in the magnesium contents.

EXAMPLE 3

Repeat the procedure of Example 1, the magnesium (4%) impregnated catalyst (SiO$_2$/Al$_2$O$_3$=90), which was used once before and regenerated with the known technique (50% of air and 50% of nitrogen, as processed for 3–4 hours, at a gross flow rate of 100 ml/min., at a temperature of 520° C.). The reactivity of the catalyst as shown before regeneration and that after regeneration is given in Table 1. Apparently indicated in the Table, the catalyst loses its activity and p-isomer selectivity after regeneration. The same kind of demerits can be seen also in the case of the catalyst which has been immersed in such solutions of phosphorous, boron or silane compounds. ET in the tables represents ethyltoluene.

TABLE 1

Magnesium-impregnated catalyst (Mg/HZSM-5)
Difference of reaction before and after regeneration

| conditions | before regeneration | after regeneration |
|---|---|---|
| Temperature (°C.) | 350 | 350 |
| Pressure (psig) | 0 | 0 |
| Feed rate, Tol | 12.8 | 12.8 |
| (WHSV) $C_2H_4$ | 0.40 | 0.41 |
| (Tol/$C_2H_4$) mole | 9.8 | 9.6 |
| $C_2H_4$ conversion (%) | 72.3 | 65.6 |
| ET Selectivity (%) | 81.1 | 83.2 |
| ET yield (%) | 58.7 | 54.6 |
| p-ET (33.7)* (%) | 72.5 | 66.8 |
| m-ET (49.9)* (%) | 27.3 | 33.0 |
| o-ET (16.3)* (%) | 0.2 | 0.2 |
| time on stream (hrs) | 16 | 14 |

*equilibrium fraction at 327° C.

EXAMPLE 4:

New vapor phase deposition process for modifying HZSM-5 catalyst to Si/ZSH-5
(I) Pulsating type deposition before the reaction:

One gram of HZSM-5 catalyst, (crystal size about 3 μm and the ratio of $SiO_2/Al_2O_3$ about 90) is placed inside a reactor and retained in the reactor for 4 hours, with an air-borne saturated steam passing at a temparature of 540° C. The reactor is then purged with saturated steam to replace the air and is cooled to 320° C. The cooling process takes about two hours. The flow rates of the aforesaid air and nitrogen entrained steam are all 600 liters/kilogram catalyst/hour.

By pulsating injection at a temperature of 350° C. with $Si(OC_2H_5)_4$ carried by nitrogen, 150 μl of $Si(OC_2H_5)_4$ is injected every two hours, until the predetermined amount has been fed. The ortho-silicate is decomposed and deposited as sediment of silicon, on the surface of the catalyst. The sediment, however, will not clog the pores of the catalyst, as a special features.

EXAMPLE 5

New vapor phase deposition process for modifying HZSM-5 catalyst to Si/HZSM-5:
(II) Pulsating type deposition during the reaction:

Repeat the procedure of Example 4, except that the pulsating injection is effected at a temperature of 350° C. The feed of material is carried by the substantially high temperature gaseous substance under reaction. 150 μl of $Si(OC_2H_5)_4$ is injected every two hours, till the required volume is supplied Silicide is deposited, after decomposition, as sediment of silicon on the surface of catalyst. The sediment, however, will not clog the pores of the catalyst, as a special feature.

EXAMPLE 6

Figure 2:
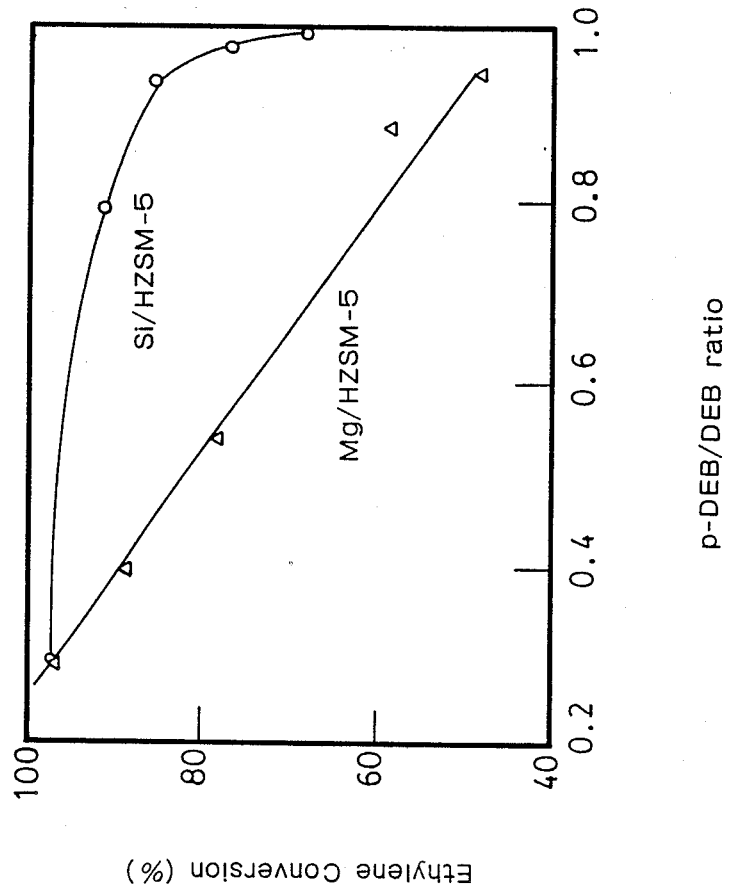

The activity and regeneration of Si/HZSM-5 catalyst as modified by vapor phase pulsating injection method:

Table 2 is indicative of the deposition during reaction. This method is better than the deposition before reaction both in activity and selectivity to the desirable product. When compared with the previous immersion catalyst, it is understood that the catalyst as modified by the deposition of silicon is preferred in regeneration and better in activity. Especially, it is note-worthy that the selectivity to product of p-ethyltoluene in ethyltoluenes (ET) is as high as over 90%. This is the best result so far achieved through the modification of catalyst. FIG. 2 shows a comparison of activity between the magnesium-immersed catalyst in general and the catalyst modified by silicon in the deposition method.

TABLE 2

The Performance of the Catalyst as Modified by Pulse Vapor Phase Silicon Deposition

| conditions | unmodified HZSM-5(90)II 1 | deposition before reaction 2 | deposition during reaction 3 | deposition during reaction 4 | after 1st regeneration | after 2nd regeneration |
|---|---|---|---|---|---|---|
| Temperature (°C.) | 350 | 349 | 350 | 350 | 350 | 350 |
| Pressure (psig) | 0 | 0 | 0 | 0 | 0 | 0 |
| feed rate, Tol | 16.7 | 16.6 | 16.7 | 16.7 | 16.7 | 16.7 |
| (WHSV) $C_2H_4$ | 0.58 | 0.62 | 0.57 | 0.57 | 0.57 | 0.58 |
| (Tol/$C_2H_4$)$_{mole}$ | 8.8 | 8.1 | 8.9 | 8.9 | 8.9 | 8.8 |
| $C_2H_4$ conversion (%) | 95.8 | 59.0 | 78.8 | 62.2 | 66.9 | 67.2 |
| ET selectivity | 77.0 | 86.5 | 83.1 | 84.1 | 83.8 | 83.7 |
| ET yield (%) | 73.8 | 51.0 | 65.5 | 52.3 | 56.1 | 56.2 |
| p-ET (33.7)*(%) | 29.3 | 92.5 | 98.3 | 99.6 | 99.4 | 99.4 |
| m-ET (49.9)*(%) | 63.7 | 7.5 | 1.3 | 0.4 | 0.6 | 0.6 |
| o-ET (16.3)*(%) | 7.0 | 0 | 0 | 0 | 0 | 0 |
| time on stream (hrs) | 16 | 20 | 29 | 45 | 12 | 17 |
| accumulated amount of $Si(OC_2H_5)_4$ added (μl) | — | 1050 | 1050 | 1500 | 1500 | 1500 |

*equilbrium fraction at 327° C.

EXAMPLE 7

Figure 3:
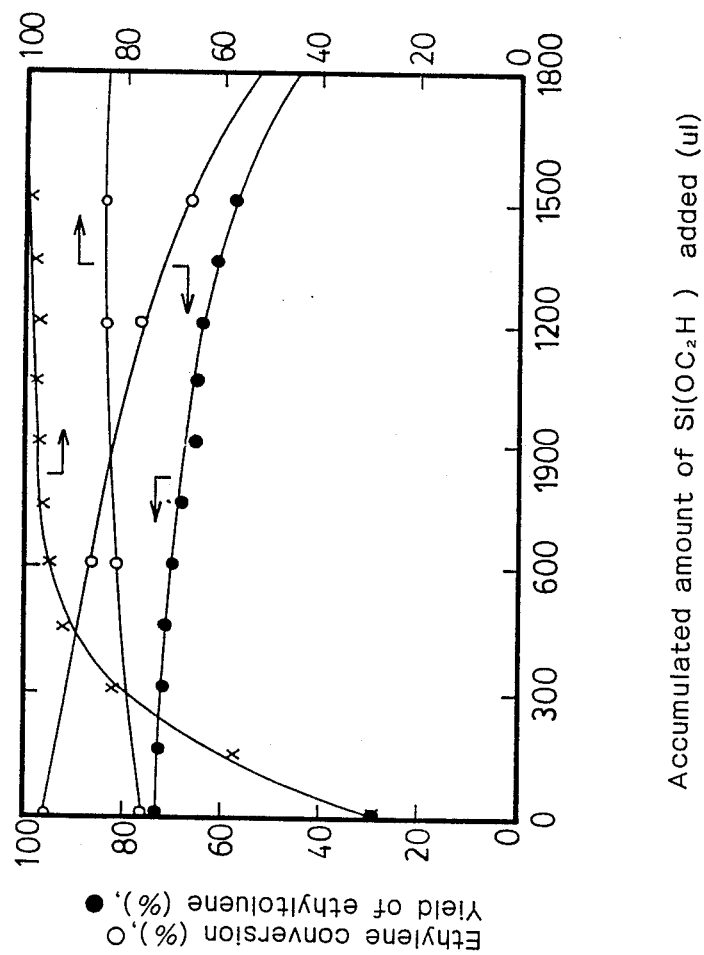

Effect of $Si(OC_2H_5)$ deposit amount upon reaction:

In accordance with the modification of catalyst as given in Example 5 under the same condition of operation given in Example 6 various effects are observed with different amount of $Si(OC_2H_5)_4$ added. As indicated in FIG. 3, almost no o-ethyltoluene is produced in the course of the reaction. Therefore, a proper adjustment of volume of $Si(OC_2H_5)_4$ to be added may result in a different ratio of p-ethyltoluene/m-ethyltoluene. The dehydrogenated product may result in polymers of different physical properties after polymerization.

EXAMPLE 8

New vapor phase deposition process for modifying HZSM-5 catalyst to Si/HZSM-5—(III) continuous deposition during reaction:

Repeat the same procedure as in Example 4, except that 2% $Si(OC_2H_5)_4$ is used in the liquid starting material (toluene or ethylbenzene). Meantime the nitrogen with saturated steam at the same mole fraction is fed into the reactor. The conditions of the reaction should be kept at:

Pressure: 1 atmosphere

Temperature: 320° C.
Feed ratio: 3.5 kg ethylbenzene/kg catalyst/hour

The product is analysed once every hour, until the fraction ratio of p-dialkylbenzene reaches 0.95, when the reaction is considered to be complete. The modification takes about 6 hours.

EXAMPLE 9

The reactivity of Si/HZSM-5 catalyst modified by continuous deposition during reaction disproportionation of ethylbenzene:

The catalyst obtained from Example 8 is used in contact with pure ethylbenzene as the feed. The reaction is to proceed under the following conditions of operations:
Pressure: 1 atmosphere
Temperature at beginning of operation: 330° C.
Feed ratio: 3.5 kg ethylbenzene/kg catalyst/hour
Temperature at the end of operation: 400° C.
Average rise of temperature per day: 3.5° C.
Cycle of regeneration of catalyst: ~20 days
The following results may be obtained:
Conversion ratio: ~20%
Fraction ratio of p-diethylbenzene: 0.98
Benzene/diethylbenzene mole ratio: 1.4

EXAMPLE 10

Figure 4:
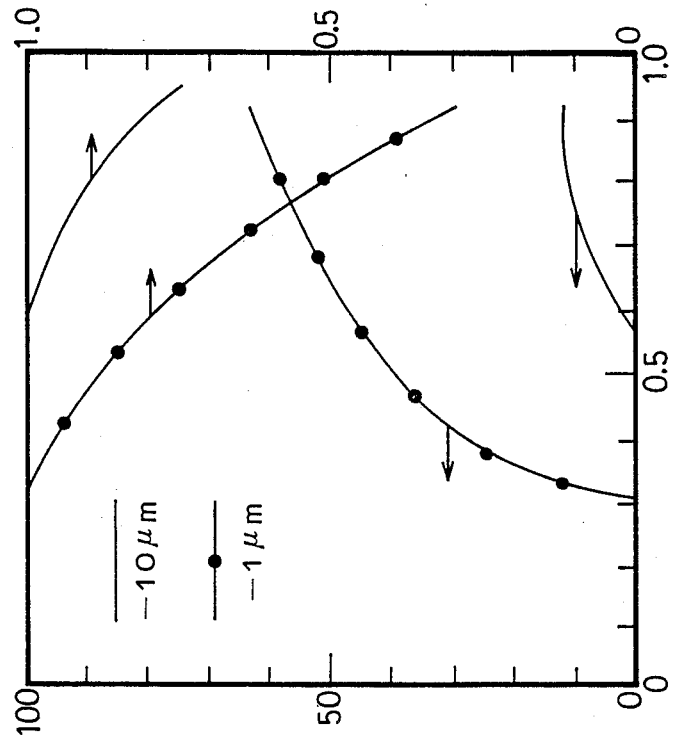
Figure 5:
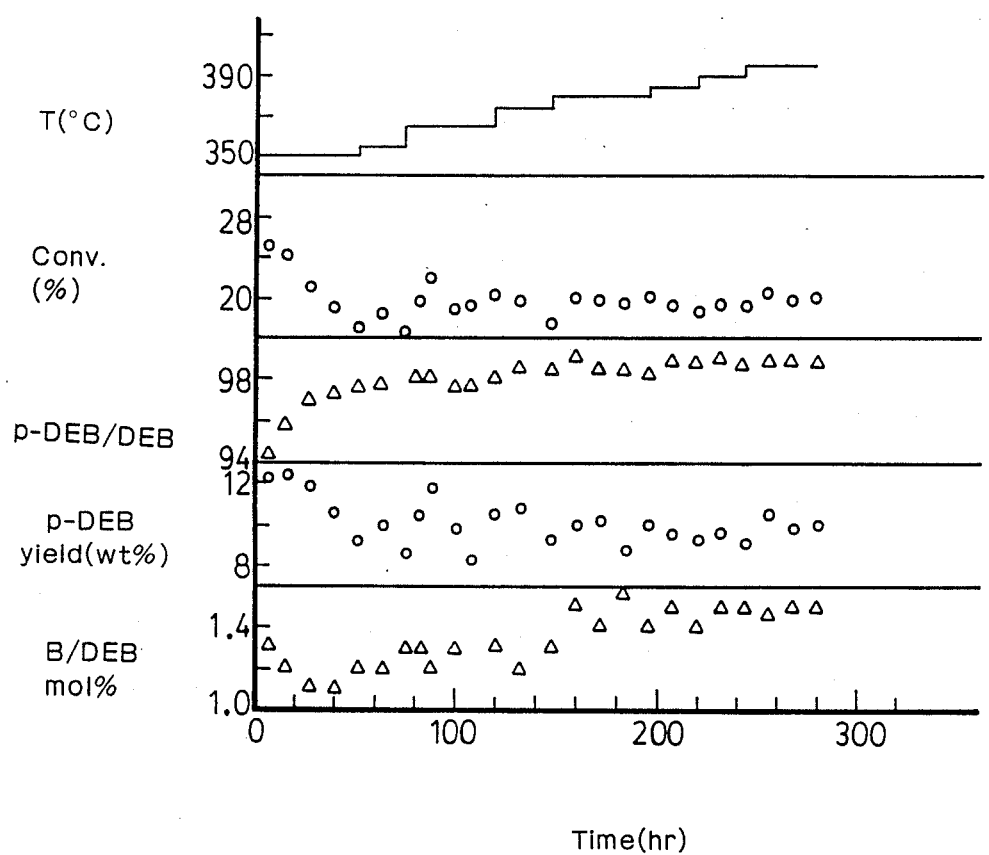
Figure 6:
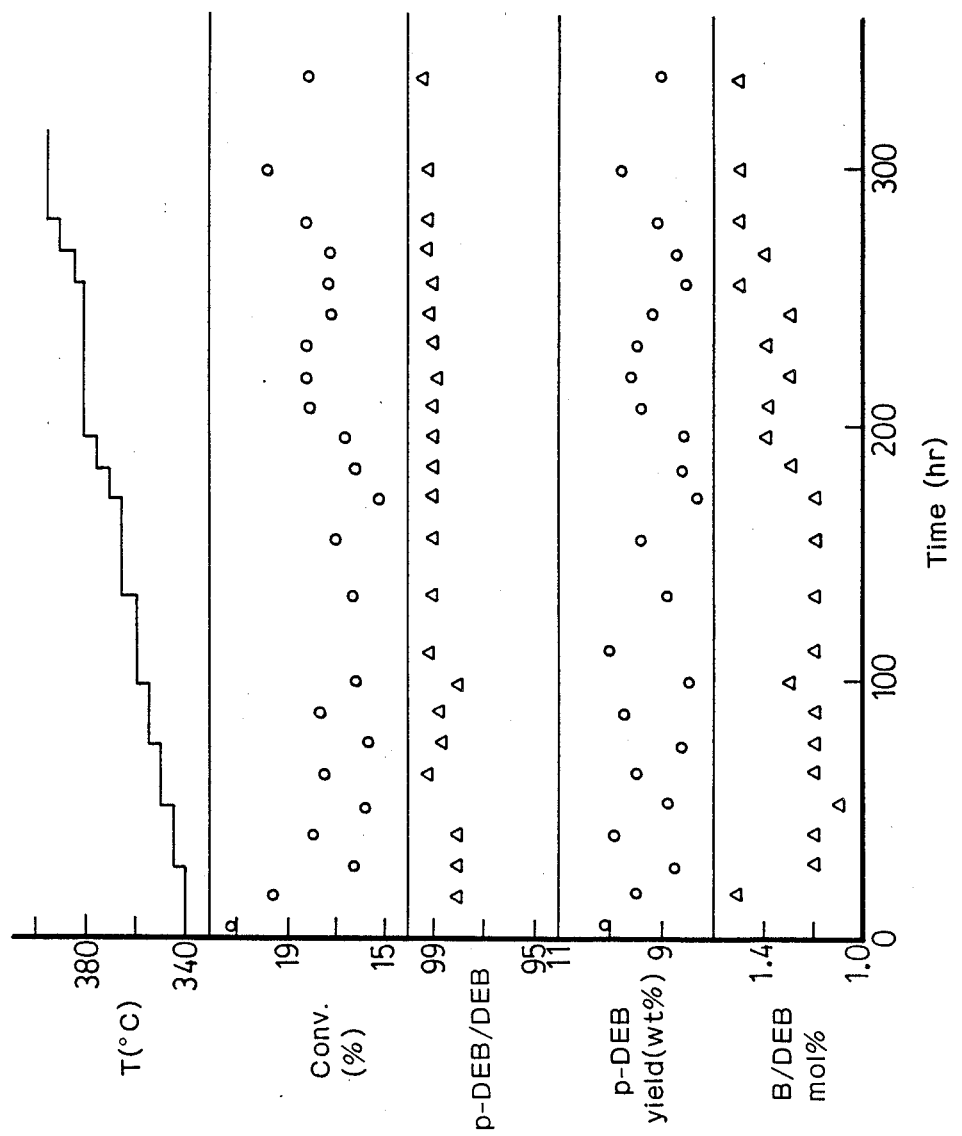
FIG. 6 Long-term test on the modified Si/HZSM-5 catalyst, after its second regeneration, in a disproportionation reaction to p-ethylbenzene (large particles, without binder)
Figure 7:
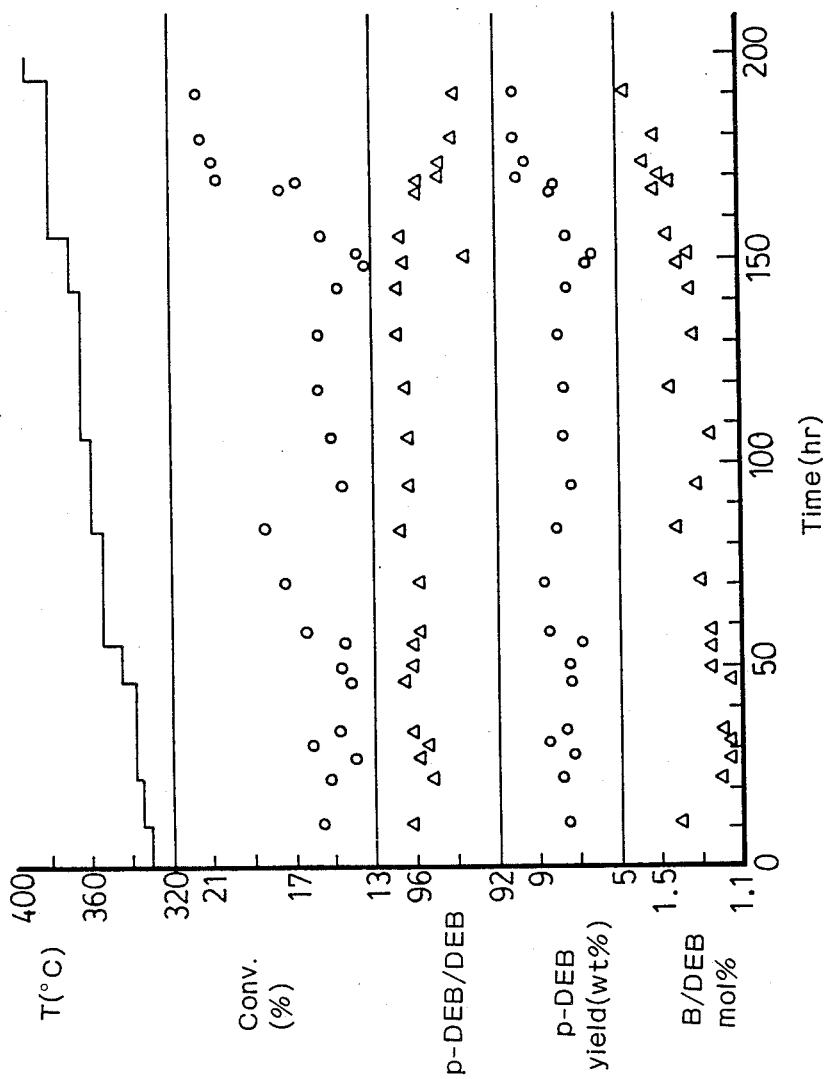
FIG. 7 Long-term test on the modified Si/HZSM-5 catalyst, in a disproportionation reaction to p-ethylbenzene, under atmospheric pressure (small particles, $\gamma$-Al$_2$O$_3$ as binder)
Figure 8:
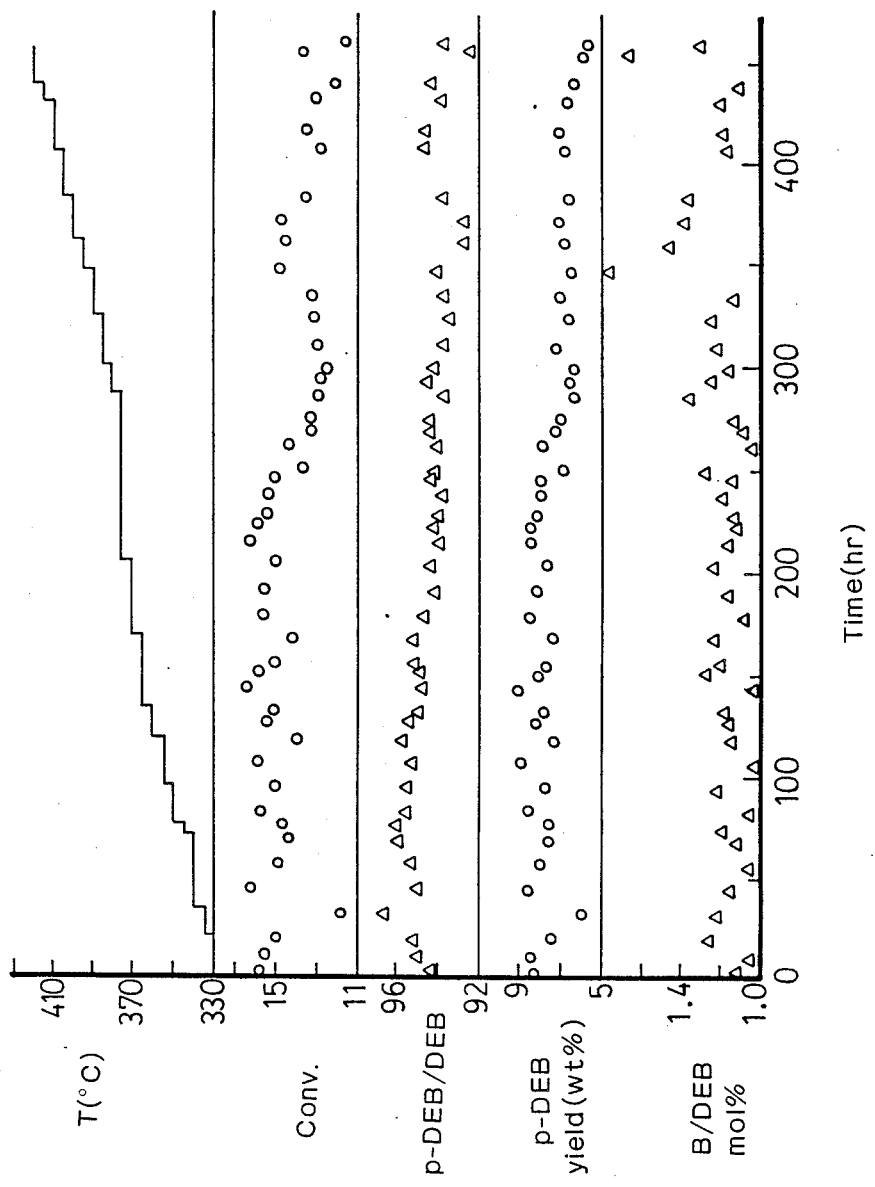
FIG. 8 Long-term test on the modified Si/HZSM-5 catalyst, in a disproportionation reaction to p-ethylbenzene, under pressure of 5 atmospheres (small particles, $\gamma$-Al$_2$O$_3$ as binder)

Effect of particle size of catalyst crystal upon its activity:

In case the particles are smaller than average (e.g. smaller than 1 μm), there will be more activated sites on the surface of the particles. As a result of being deposited on by silicon, the activity will greatly be reduced. FIG. 4 shows the relationship between the conversion and selectivity to product and volume of sediment of silicon in the course of the modification of ZSM-5 catalyst. As indicated in the Figure, the bigger the particles, the better the effect of modification.

EXAMPLE 11

Effect of catalyst binder:

The decomposition reactivity of Si(OC$_2$H$_5$)$_4$ varies with different bonding agent. The selection of proper bonding agent may result in a better reaction effect. Table 3 shows the temperature of decomposition of Si(OC$_2$H$_5$)$_4$ on different kinds of bonding material and HZSM-5 itself. Among those tested, Kieselguhr is the most inert one and, therefore, should be the best bonding material.

TABLE 3
A comparison of reactivity of Si(OEt)$_4$ on different kinds of binder

| | Temperature, ° C. | |
|---|---|---|
| HZSM-5 | <180 | Si(OEt)$_4$ partial pressure: 15 mmHg |
| SiO$_2$—Al$_2$O$_3$ | <180 | |
| γ-Al$_2$O$_3$ | ~230 | Time of Contact: 5 sec |
| Kieselguhr | >320 | Conversion: 50% |

EXAMPLE 12

New vapor phase deposition process for modifying HZSM-5 catalyst to Si/HZSM-5—(IV)—continuous deposition before reaction:

Conventional catalyst ZSM-5 of small crystal particles (smaller than 1 μm) is usually bonded together to pellet or extrudates with γ-Al$_2$O$_3$ as the binder. With such a catalyst the conversion obtained under the operational conditions given in Example 9, is merely 1%. An improved process may comprise:
Feed: 50% toluene+45% methanol+5% Si(OC$_2$H$_5$)$_4$ (percentage by volume), in combination with nitrogen and steam of identical mole ratio.
Feed rate: 3.5 kg/kg catalyst/hour
Pressure: 1 atmosphere
Temperature: 180° C. (2 hours), with an elevation of temperature by 10° C. per hour until it comes up to 230° C.

EXAMPLE 13

A comparison of activity in prolonged reaction of different kinds of catalysts:

A comparative study in the reaction of modified large-particle catalyst without bonding material as described in Example 8 in contrast with the small-particle catalyst, as modified on the basis of the method given in Example 12 is made. The result of the comparison is given in Table 4.

TABLE 4
A comparison of reactivity of different kinds of catalysts as modified with different methods

| Category of Catalysts | Large Particles | Small particles with binder | Small particles with binder |
|---|---|---|---|
| Reaction Temperature | 320° C.~390° C. | 320° C.~390° C. | 320° C.~400° C. |
| Reaction Pressure | 1 | 1 | 5 |
| Average Conversion Ratio | 20% | 16.8% | 14.9% |
| Average Yield of p-ethylbenzene | 10% | 8.2% | 7.9% |
| Purity of p-diethylbenzene/ diethylbenzenes | 98% | 95.9% | 94.8% |
| Average Mole Ratio of Benzene/diethylbenzene | 1.4 | 1.38 | 1.19 |

EXAMPLE 14

Toluene in disproportionation reaction over Si/HZSM-5 catalyst:

The catalyst as modified according to Example 12 (the catalyst contains 35% γ-Al$_2$O$_3$) is used in the disproportion of toluene. The selectivity to p-xylene as the major product is greatly enhanced in xylenes and elevates with the increase of deposited amount of Si(OC$_2$H$_5$)$_4$. Table 5 shows the increase in deposition of silicide may raise the selectivity to product of p-xylene up to 90% or over, with no o-xylene yielded.

TABLE 5

Utilization of Si/HZSM-5 disproportionation of toluene

| Catalyst | HZSM-5 | | | Si/HZSM-5* | | Si/HZSM-5 | | |
|---|---|---|---|---|---|---|---|---|
| Run No. | 1 | 2 | 3 | 1 | 2 | 1 | 2 | 3 |
| Temp. (°C.) | 400 | 450 | 500 | 450 | 500 | 450 | 500 | 530 |
| Pressure (atm) | 1 | 1 | 1 | 1 | 1 | 1 | 1 | 1 |
| WHSV, total | 3.5 | 3.5 | 3.5 | 3.5 | 3.5 | 3.8 | 3.8 | 3.8 |
| Conversion (%) | 3.05 | 8.12 | 17.26 | 8.8 | 17.78 | 2.92 | 5.48 | 7.6 |
| Selectivity to Product (wt %) | | | | | | | | |
| $C_1$–$C_5$ | 0.04 | 0.12 | 0.08 | 0.19 | 0.25 | 0 | 0 | 0 |
| Benzene | 42.01 | 42.54 | 44.85 | 44.80 | 48.86 | 43.57 | 45.26 | 46.91 |
| p-xylene | 15.11 | 14.89 | 14.34 | 30.38 | 27.71 | 51.32 | 43.90 | 39.56 |
| m-xylene | 30.67 | 29.86 | 28.39 | 18.21 | 17.65 | 5.11 | 9.48 | 11.76 |
| o-xylene | 12.17 | 12.46 | 12.21 | 4.45 | 4.74 | 0 | 1.16 | 1.77 |
| $C_9$ | — | 0.13 | 0.13 | 1.97 | 0.78 | 0 | 0 | 0 |
| xylene isomer (%) | | | | | | | | |
| p-xylene | 26.08 | 25.97 | 26.10 | 57.27 | 54.78 | 90.95 | 80.18 | 74.51 |
| m-xylene | 52.92 | 52.30 | 51.68 | 34.34 | 34.86 | 9.05 | 17.70 | 22.14 |
| o-xylene | 21.00 | 21.73 | 22.22 | 8.4 | 9.36 | 0 | 2.12 | 3.34 |

*Sediment of Si is 0.176 gram/g catalyst
Sediment of Si is 0.226 gram/g catalyst

EXAMPLE 15

Alkylation of methanol and toluene over Si/HZSM-5 catalyst:

The catalyst (containing 35% γ-$Al_2O_3$) as modified according to Example 12 is utilized in alkylation of methanol and toluene so as to elevate the selectivity to p-xylene in major products. Deposit of Si is 0.176 gram/g catalyst. The results of the reaction are given reported in Table 6.

TABLE 6

Utilization of Si/HZSM-5 in alkylation of methanol and toluene

| Catalyst | HZSM-5 | | Si/HZSM-5 | | |
|---|---|---|---|---|---|
| Run No. | 1 | 2 | 1 | 2 | 3 |
| Temp. (°C.) | 350 | 400 | 400 | 450 | 500 |
| Pressure (atm) | 1 | 1 | 1 | 1 | 1 |
| WHSV, total | 3.5 | 3.5 | 3.5 | 3.5 | 3.5 |
| Toluene/methanol mole ratio | 4/1 | 4/1 | 4/1 | 4/1 | 4/1 |
| Conversion | | | | | |
| Toluene | 7.58 | 12.27 | 8.64 | 11.1 | 13.55 |
| Methanol | ~100 | ~100 | ~100 | ~100 | ~100 |
| Selectivity to Product (wt %) | | | | | |
| $C_1$–$C_4$ | 2.16 | 2.69 | 4.12 | 3.10 | 1.34 |
| Benzene | 8.06 | 13.08 | 17.58 | 18.36 | 20.23 |
| Ethylbenzene | 1.46 | 0.93 | — | — | — |
| Xylene | 66.50 | 67.83 | 67.30 | 72.27 | 74.05 |
| Ethyltoluene | 20.24 | 10.97 | 11.00 | 4.52 | 1.82 |
| Diethylbenzene | 1.57 | 4.40 | — | 1.75 | 2.56 |
| Xylene isomer (%) | | | | | |
| p-xylene | 29.72 | 26.89 | 71.15 | 68.23 | 63.42 |
| m-xylene | 49.55 | 51.52 | 20.29 | 20.71 | 24.35 |
| o-xylene | 20.73 | 21.60 | 8.56 | 11.05 | 12.23 |

EXAMPLE 16

Alkylation of ethylene and ethylbenzene over Si/HZSM-5 catalyst:

The catalyst (containing 35% γ-$Al_2O_3$) as modified according to Example 12 is utilized in alkylation of ethylene and ethylbenzene, at a temperature of 320° C. The modified catalyst having Si deposit amounted to 0.176 g/g catalyst; whereby, the selectivity to product p-diethylbenzene reaches as high as 94%, with no o-diethylbenzene isomer yielded. The results of the reaction are given in Table 7.

TABLE 7

Utilization of Si/HZSM-5 for alkylation of ethylene and ethylbenzene

| Catalyst | HZSM-5 | | | Si/HZSM-5 | | |
|---|---|---|---|---|---|---|
| Run No. | 1 | 2 | 3 | 1 | 2 | 3 |
| Temp. (°C.) | 320 | 360 | 400 | 320 | 360 | 400 |
| Pressure (atm) | 1 | 1 | 1 | 1 | 1 | 1 |
| Ethylbenezene WHSV | 4.99 | 4.99 | 4.99 | 5 | 5 | 5 |
| Ethylene | 0.18 | 0.18 | 0.18 | 0.18 | 0.18 | 0.18 |
| Ethylbenzene/ | 8.43 | 8.43 | 8.43 | 8.45 | 8.45 | 8.45 |

TABLE 7-continued

Utilization of Si/HZSM-5 for alkylation of ethylene and ethylbenzene

| Catalyst | HZSM-5 | | | Si/HZSM-5 | | |
|---|---|---|---|---|---|---|
| Run No. | 1 | 2 | 3 | 1 | 2 | 3 |
| ethylene mole ratio | | | | | | |
| Conversion | | | | | | |
| Ethylbenzene | 7.46 | 12.95 | 24.12 | 6.89 | 9.32 | 13.27 |
| Ethylene | 75.78 | 49.58 | ~* | 70 | 44.58 | 5 |
| Selectivity to product (wt %) | | | | | | |
| $C_1$–$C_5$ | 5.45 | 5.03 | 2.88 | 2.26 | 2.87 | 3.04 |
| Benzene | 17.95 | 33.06 | 47.66 | 12.18 | 25.63 | 45.33 |
| Toluene | 6.29 | 5.08 | 5.09 | 4.47 | 3.74 | 3.71 |
| Xylene | 3.42 | 2.93 | 4.28 | 4.31 | 2.80 | 1.96 |
| Ethyltoluene | 2.43 | 1.88 | 1.45 | 0 | 0.48 | 0.64 |
| Diethylbenzene | 60.43 | 50.42 | 37.83 | 76.77 | 64.47 | 45.32 |
| High-carbon compounds | 4.02 | 1.60 | 0.82 | 0 | 0 | 0 |
| Diethylbenzene isomer (%) | | | | | | |
| p-diethylbenzene | 47.42 | 46.33 | 46.38 | 93.97 | 91.90 | 89.12 |
| m-diethylbenzene | 52.58 | 53.67 | 53.62 | 6.03 | 8.10 | 10.88 |
| o-diethylbenzene | 0 | 0 | 0 | 0 | 0 | 0 |

*The ethyl group on the ethylbenzene is liable to break, at high temperature, and split into ethylene.

EXAMPLE 17

The trans-alkylation of toluene and ethylbenzene over Si/HZSM-5 catalyst:

The HZSM-5 catalyst (containing 35% γ-$Al_2O_3$) is modified according to Example 12, thus obtaining Si/HZSM-5 catalyst having the Si deposit of 0.107 g/g catalyst. The modified catalyst is utilized to carry out the trans-alkylation of toluene and ethylbenzene. The results of the reaction are given in Table 8.

On the basis of the method given in Example 9, the catalyst which is modified according to the aforesaid method, is utilized to proceed the disproportionation of ethylbenzene, under the following conditions of reaction:

Temperature: 320° C.
Pressure: 15 psia
WHSV: 3.95 kg/kg catalyst/hour
The results of the reaction are given in Table 9.

TABLE 8

The trans-alkylation of toluene and ethylbenzene over Si/HZSM-5 catalyst

| Catalyst | HZSM-5 | | | | | Si/HZSM-5 | | |
|---|---|---|---|---|---|---|---|---|
| Run No. | 1 | 2 | 3 | 4 | 5 | 1 | 2 | 3 |
| Conditions | | | | | | | | |
| Temp. °C. | 300 | 320 | 320 | 360 | 400 | 320 | 360 | 400 |
| Pressure, atm. | 1 | 1 | 1 | 1 | 1 | 1 | 1 | 1 |
| WHSV | 4 | 4 | 4 | 4 | 4 | 4 | 4 | 4 |
| Toluene/EB mole ratio | 1 | 1 | 1.5 | 1 | 1 | 1 | 1 | 1 |
| Conversion, % | | | | | | | | |
| Toluene | 8.55 | 11.65 | 9.66 | 16.74 | 17.70 | 7.29 | 9.67 | 8.12 |
| Ethylbenzene | 15.59 | 25.36 | 28.19 | 41.91 | 59.19 | 16.98 | 29.55 | 42.43 |
| Selectivity to Product, wt % | | | | | | | | |
| $C_1$–$C_5$ | 0.24 | 0.34 | 0.40 | 1.20 | 2.64 | 0.93 | 0.94 | 1.73 |
| Benzene | 39.77 | 40.43 | 39.98 | 43.79 | 54.02 | 41.27 | 47.04 | 59.61 |
| Xylene | 0.38 | 1.57 | 1.44 | 2.28 | 3.54 | 0.27 | 0.35 | 0.68 |
| Ethyltoluene | 33.33 | 25.53 | 41.38 | 35.92 | 28.87 | 35.40 | 34.54 | 27.56 |
| Diethylbenzene | 26.28 | 22.13 | 16.80 | 16.81 | 10.93 | 22.13 | 17.12 | 10.42 |
| Diethylbenzene isomer, % | | | | | | | | |
| para | 38.55 | 38.92 | 37.27 | 37.23 | 29.28 | 90.01 | 87.18 | 75.00 |
| meta | 61.45 | 61.08 | 62.43 | 62.77 | 70.72 | 9.99 | 12.82 | 25.00 |
| ortho | 0 | 0 | 0 | 0 | 0 | 0 | 0 | 0 |
| Ethyltoluene/DEB wt ratio | 1.27 | 1.61 | 2.46 | 2.14 | 2.64 | 1.60 | 2.02 | 2.64 |
| mole ratio | 1.42 | 1.79 | 2.75 | 2.39 | 2.95 | 1.79 | 2.25 | 2.95 |

Ethyltoluene/diethylbenzene

EXAMPLE 18

The catalyst is modified, under the following conditions of reaction, according to the procedure given in Example 12:

Feed: Toluene: methanol: $Si(OCH_3)_4$ = 50:47:3 (percentage by volume), in combination with nitrogen and steam with same mole ratio.
Temperature: 180° C.
Pressure: 15 psia
WHSV: 10 kg/kg catalyst/hour

TABLE 9

Results of Reaction of Example 18

| | Duration for modification of Catalyst (hour) | | After Regeneration Time on Stream (hour) | |
|---|---|---|---|---|
| | 3 | 4 | 1.5 | 9.5 |
| Conversion (%) | 15.8 | 11.53 | 18.31 | 10.95 |
| Selectivity to Product (wt. %) | | | | |
| Diethylbenzene | 48.57 | 50.67 | 49.70 | 54.46 |
| Benzene | 39.11 | 38.57 | 40.85 | 39.22 |
| Diethylbenzene isomer (%) | | | | |
| p-diethylbenzene | 91.95 | 97.00 | 88.72 | 96.49 |

TABLE 9-continued

Results of Reaction of Example 18

|  | Duration for modification of Catalyst (hour) | | After Regeneration Time on Stream (hour) | |
|---|---|---|---|---|
|  | 3 | 4 | 1.5 | 9.5 |
| m-diethylbenzene | 8.05 | 3.00 | 9.95 | 3.35 |
| o-diethylbenzene | 0 | 0 | 1.33 | 0.16 |

EXAMPLE 19

The catalyst is modified, under the following conditions of reaction, corresponding to Example 12

Feed: Toluene: methanol: $Si(OC_4H_9)_4 = 50:47:3$ (percentage by volume), in combination with nitrogen and steam with same mole ratio.
Temperature: 180° C.
Pressure: 15 psia
WHSV: 10 kg/kg catalyst/hour Further in correspondence with Example 9, the catalyst which is modified according to the aforesaid method, is utilized to proceed disproportionation of ethylbenzene, under the following conditions of reaction:
Temperature: 320° C.
Pressure: 15 psia
WHSV: 4.0 kg/kg catalyst/hour
The results of the reaction are given in Table 10

TABLE 10

Results of Reaction of Example 19

|  | Duration Time for Modification of Catalyst (hour) | | | After Regeneration Time on Stream (hour) | |
|---|---|---|---|---|---|
|  | 2 | 4 | 6 | 1 | 4 |
| Conversion (%) | 19.08 | 14.83 | 8.33 | 9.55 | 8.42 |
| Selectivity to Product (wt %) | | | | | |
| Diethylbenzene | 58.54 | 50.53 | 49.27 | 51.13 | 54.09 |
| Benzene | 37.80 | 37.72 | 38.22 | 40.29 | 39.47 |
| Diethylbenzene isomer (%) | | | | | |
| p-diethylbenzene | 67.28 | 81.76 | 92.22 | 86.46 | 91.93 |
| m-diethylbenzene | 32.72 | 18.24 | 7.78 | 13.54 | 8.07 |
| o-diethylbenzene | 0 | 0 | 0 | 0 | 0 |

EXAMPLE 20

The catalyst as modified according to Example 19 is utilized in the disproportionation of ethylbenzene, under various conditions, for 6 hours. The results of the reaction are given in Table 11.

TABLE 11

Results of the reaction in Example 20

| Conditions | | | | | |
|---|---|---|---|---|---|
| Temp. (°C.) | 320 | 360 | 360 | 360 | 400 |
| Pressure (psig) | 250 | 250 | 250 | 250 | 250 |
| WHSV | 3.95 | 3.95 | 8.41 | 17.34 | 17.34 |
| Conversion (%) | 20.46 | 35.26 | 18.0 | 8.55 | 12.96 |
| Selectivity to product (wt %) | | | | | |
| Diethylbenzene | 54.38 | 37.78 | 52.48 | 51.17 | 50.40 |
| Benzene | 37.33 | 44.54 | 38.91 | 38.42 | 39.57 |
| Diethylbenzene isomer (%) | | | | | |
| p-diethylbenzene | 66.36 | 58.46 | 78.41 | 85.65 | 75.21 |
| m-diethylbenzene | 31.03 | 36.64 | 20.68 | 14.35 | 22.31 |
| o-diethylbenzene | 2.61 | 1.90 | 0.91 | 0 | 2.48 |

EXAMPLE 21

The catalyst, which is modified for 6 hours according to the method given in Example 19, is utilized to carry out the disproportionation of ethylbenzene under various conditions as stated in the following table. The results of the reaction are given in Table 12:

TABLE 12

Results of reaction in Example 21

|  | RUN NO. | | | |
|---|---|---|---|---|
|  | 1 | 2 | 3 | 4 |
| CONDITION OF REACTION | | | | |
| TEMP. (°C.) | 320 | 360 | 360 | 360 |
| PRESS. (PSIG) | 750 | 750 | 750 | 750 |
| WHSV | 4.25 | 4.16 | 8.91 | 17.51 |
| EB CONV. (%) | 12.34 | 20.69 | 12.30 | 6.83 |
| SELECTIVITY TO PROD. (WT %) | | | | |
| B | 38.12 | 39.86 | 41.34 | 38.85 |
| DEB | 53.98 | 45.83 | 51.02 | 55.57 |
| ISOMER SELECTIVITIY (%) | | | | |
| P-DEB | 77.83 | 70.60 | 80.36 | 85.15 |
| M-DEB | 20.67 | 28.11 | 19.64 | 14.85 |
| O-DEB | 1.49 | 1.29 | 0 | 0 |

We claim:
1. A process for the preparation of p-alkyl benzene by contacting a mixture of monoalkyl benzene and $C_1$–$C_4$ alkene or alkanol with a Si/HZSM-5 zeolite catalyst, characterized in that:
said Si/HZSM-5 zeolite is produced by depositing silicon sediment obtained by decomposing in vapor phase a silicon source of tetra alkyl orthosilicate or tetraalkoxy silane of the formula Si(OR)$_4$ (in which R represents alkyl group containing 1–4 carbon atoms) on the surface of an HZSM-5 catalyst, said silicon sediment substantially not clogging the pores of said HZSM-5 catalyst.

2. A process according to claim 1, wherein R represents ethyl.

3. A process according to claim 1, wherein the vapor phase deposition is effected with a pulsating type of deposition before the reaction and pulsating type during the reaction, and continuous type before the reaction and the continuous type during the reaction.

4. A process according to claim 1, wherein said monoalkyl benzene is selected from the group consisting of toluene and ethyl benzene.

5. A process according to claim 1, wherein said $C_1$–$C_4$ alkene is ethylene.

6. A process according to claim 1, wherein said alkanol is selected from the group consisting of methanol and ethanol.

7. A process according to claim 1, which is conducted under the conversion conditions of a temperature between 200° and 600° C., a pressure between 15 and 1000 psia and a WHSV between 0.5 and 100.

* * * * *